United States Patent
Safai et al.

(10) Patent No.: US 10,578,565 B2
(45) Date of Patent: Mar. 3, 2020

(54) X-RAY INSPECTION SYSTEM FOR PIPES

(71) Applicant: The Boeing Company, Chicago, IL (US)

(72) Inventors: Morteza Safai, Newcastle, WA (US); Gary Ernest Georgeson, Tacoma, WA (US)

(73) Assignee: The Boeing Company, Chicago, IL (US)

(*) Notice: Subject to any disclaimer, the term of this patent is extended or adjusted under 35 U.S.C. 154(b) by 214 days.

(21) Appl. No.: 15/701,244

(22) Filed: Sep. 11, 2017

(65) Prior Publication Data

US 2019/0079031 A1 Mar. 14, 2019

(51) Int. Cl.

| | |
|---|---|
| *G01N 23/203* | (2006.01) |
| *G01N 23/083* | (2018.01) |
| *G01N 23/02* | (2006.01) |
| *G01N 23/06* | (2018.01) |
| *G01B 15/02* | (2006.01) |
| *G01N 23/18* | (2018.01) |
| *G01N 23/20* | (2018.01) |

(52) U.S. Cl.
CPC .......... *G01N 23/203* (2013.01); *G01B 15/02* (2013.01); *G01N 23/02* (2013.01); *G01N 23/06* (2013.01); *G01N 23/083* (2013.01); *G01N 23/18* (2013.01); *G01N 23/20083* (2013.01); *G01N 2223/628* (2013.01)

(58) Field of Classification Search
CPC ...... G01N 23/203; G01N 23/06; G01N 23/02; G01N 29/225; G01N 29/265; G01N 23/20083; G01N 29/043; G01N 23/18; G01N 23/083; G01N 2291/2634; G01N 2223/628; G01B 15/02
See application file for complete search history.

(56) References Cited

U.S. PATENT DOCUMENTS

| | | | |
|---|---|---|---|
| 5,007,291 A | 4/1991 | Walters et al. | |
| 5,420,427 A * | 5/1995 | Morgan | G01N 23/18 250/358.1 |
| 6,106,152 A | 8/2000 | Thunberg | |

(Continued)

FOREIGN PATENT DOCUMENTS

| | | |
|---|---|---|
| DE | 4302286 C1 | 6/1994 |
| GB | 2211708 A | 7/1989 |

(Continued)

OTHER PUBLICATIONS

European Patent Office Extended Search Report, dated Feb. 28, 2019, regarding Application No. 18190337.8, 9 pages.

(Continued)

*Primary Examiner* — Michael C Bryant
(74) *Attorney, Agent, or Firm* — Yee & Associates, P.C.

(57) ABSTRACT

A method and system for scanning an elongate structure. A scanner in a scanning system is moved axially along the elongate structure using a translating structure in the scanning system. The elongate member is scanned axially as the scanner moves axially along the elongate structure. The scanner is moved rotationally around the elongate structure at a location in which an inconsistency is detected at the location during an axial scan. The elongate structure is scanned rotationally at the location while the scanner moves rotationally around the elongate structure.

27 Claims, 8 Drawing Sheets

(56) References Cited

U.S. PATENT DOCUMENTS

| | | | |
|---|---|---|---|
| 8,759,780 B2 | 6/2014 | Dobbs | |
| 9,709,514 B2 | 7/2017 | Edwards et al. | |
| 2005/0041775 A1* | 2/2005 | Batzinger | G01N 23/04 378/59 |
| 2011/0168900 A1* | 7/2011 | Dobbs | G01B 15/02 250/360.1 |

FOREIGN PATENT DOCUMENTS

| | | |
|---|---|---|
| RU | 2496106 C1 | 10/2013 |
| WO | WO2011023960 A1 | 3/2011 |
| WO | WO2011045563 A1 | 4/2011 |
| WO | WO2015138329 A1 | 9/2015 |
| WO | WO2015166266 A1 | 11/2015 |

OTHER PUBLICATIONS

European Patent Office Extended Search Report, dated Mar. 8, 2019, regarding Application No. 18190331.1, 7 pages.

"Twomey, "Inspection Techniques for Detecting Corrosion Under Insulation," Inspectioneering Journal Nov./Dec. 1996, accessed Aug. 8, 2017, 6 pages. https://inspectioneering.com/journal/1996-11-01/116/inspection-techniques-for-dete".

Georgeson et al., "High Speed Pipe Inspection System," U.S. Appl. No. 15/701,301, filed Sep. 11, 2017, 56 pages.

\* cited by examiner

X-RAY INSPECTION SYSTEM FOR PIPES

CROSS-REFERENCE TO RELATED APPLICATION

This application is related to U.S. patent application entitled "High Speed Pipe Inspection System,", Ser. No. 15/701,301, now U.S. Pat. No. 10,502,697 filed even date hereof, and incorporated herein by reference in its entirety.

BACKGROUND INFORMATION

1. Field

The present disclosure relates generally to inspection systems and, in particular, to nondestructive pipe inspection. Still more particularly, the present disclosure relates to a method, apparatus, and system for inspecting insulated pipes.

2. Background

Pipes are used in many industries to transport fluids. For example, the oil and gas industry uses pipes to transport oil and gas. Pipes for transporting oil are made from steel or plastic and are usually buried. The oil is moved through the pipes by pump stations along a pipeline.

Natural gas and similar gas fuels are pressurized into liquid form. Natural gas pipes are often constructed of carbon steel. As another example, district heating or tele-heating systems use a network of insulated pipes which transport heated water, pressurized hot water, or sometimes steam to a customer.

Water supply systems also employ pipes to transport drinking water to customers. Pumps pressurize potable water that flows through pipes to deliver water for consumption.

Pipe inspections are performed to determine the condition of the pipes. For example, inspection may be made to determine whether obstructions, corrosion, or other inconsistencies are present in the pipes. Inspections also may be performed to determine wall thickness, weld quality, as well as other parameters. The inspections involve nondestructive testing and may be performed in a number of different ways. For example, inspections may be made using video. This type of inspection, however, involves introducing a device into the pipes. Another type of inspection uses x-rays. This type of testing allows for the inspection from the exterior of the pipe.

One manner in which current x-ray inspections are performed is by hand. A human operator moves an x-ray scanning system along the pipe to perform the inspection. With insulated pipes, x-rays are directed through the pipe from a source on one side of the pipe and detected by a detector on the opposite side of the pipe to generate an image. In many cases, with insulated pipes, the source is then moved to the other side of the pipe and another image is generated.

A pipe for transporting oil may extend for hundreds of miles. Inspecting hundreds of miles of pipe is a time-consuming and tedious process using current techniques. Further, identifying corrosion under insulation (CUI) is often more difficult than desired. Corrosion occurring under insulation may be difficult to identify. For example, an insulation covering the pipe may mask the corrosion. Removing the insulation for inspection to check the surface condition of a pipe and replacing the insulation is undesirable because of the cost and time lost.

Profile radiography is a technique that may be used to inspect insulated pipes. X-rays are sent through a small section of a pipe wall. A comparator block is also included in the transmission which is used to calculate the wall thickness of the pipe. This type of technique is useful, but often becomes challenging in a pipe system having pipes over 10 inches in diameter.

Therefore, it would be desirable to have a method and apparatus that take into account at least some of the issues discussed above, as well as other possible issues. For example, it would be desirable to have a method and apparatus that overcome a technical problem with scanning an insulated pipe for inconsistencies with a desired level of efficiency.

SUMMARY

An embodiment of the present disclosure provides a scanning system. The scanning system comprises a translating structure, a scanner, and a controller. The translating structure is configured to move axially and rotationally on an elongate structure. The scanner is connected to the translating structure. The controller is in communication with the translating structure and the scanner. The controller controls the translating structure to move axially along the elongate structure while the scanner performs an axial scan of the elongate structure and controls the translating structure to move rotationally around the elongate structure while the scanner performs a rotational scan of the elongate structure.

Another embodiment of the present disclosure provides an x-ray scanning system. The x-ray scanning system comprises a mobile scanning arm, an x-ray scanner, and a controller. The controller is in communication with the mobile scanning arm and the x-ray scanner. The controller moves the mobile scanning arm axially such that the x-ray scanner performs an axial scan and moves the mobile scanning arm rotationally such that the x-ray scanner performs a rotational scan.

Yet another embodiment of the present disclosure provides a method for scanning an elongate structure. A scanner in a scanning system moves axially along the elongate structure using a translating structure in the scanning system. The elongate member is scanned axially as the scanner moves axially along the elongate structure. The scanner moves rotationally around the elongate structure at a location in which an inconsistency is detected at the location during an axial scan. The elongate structure is scanned rotationally at the location while the scanner moves rotationally around the elongate structure.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative embodiments recognize and take into account one or more different considerations. For example, the illustrative embodiments recognize and take into account that it would be desirable to have a method, apparatus, and system that automatically scans an elongate structure, such as a pipe.

The illustrative embodiments recognize and take into account that a rail or track system may be attached to a pipe on which an x-ray scanner may be moved. The illustrative embodiments recognize and take into account that this type of scanning typically only provides for scanning in an axial direction, a direction along an axis extending centrally through the pipe. The illustrative embodiments recognize and take into account that this type of scanning system still takes more time than desired to attach and remove a track from the pipe.

Thus, the illustrative embodiments provide a method, apparatus, and system for scanning an elongate structure. One illustrative example provides a scanning system comprising a translating structure, a scanner, and a controller. The translating structure is configured to move axially and rotationally along an elongate structure. The scanner is connected to the translating structure. The controller is in communication with the translating structure and the scanner. The controller controls the translating structure to move axially along the elongate structure while the scanner performs an axial scan of the elongate structure and controls the translating structure to move rotationally around the elongate structure while the scanner performs a rotation scan of the elongate structure.

Figure 1:
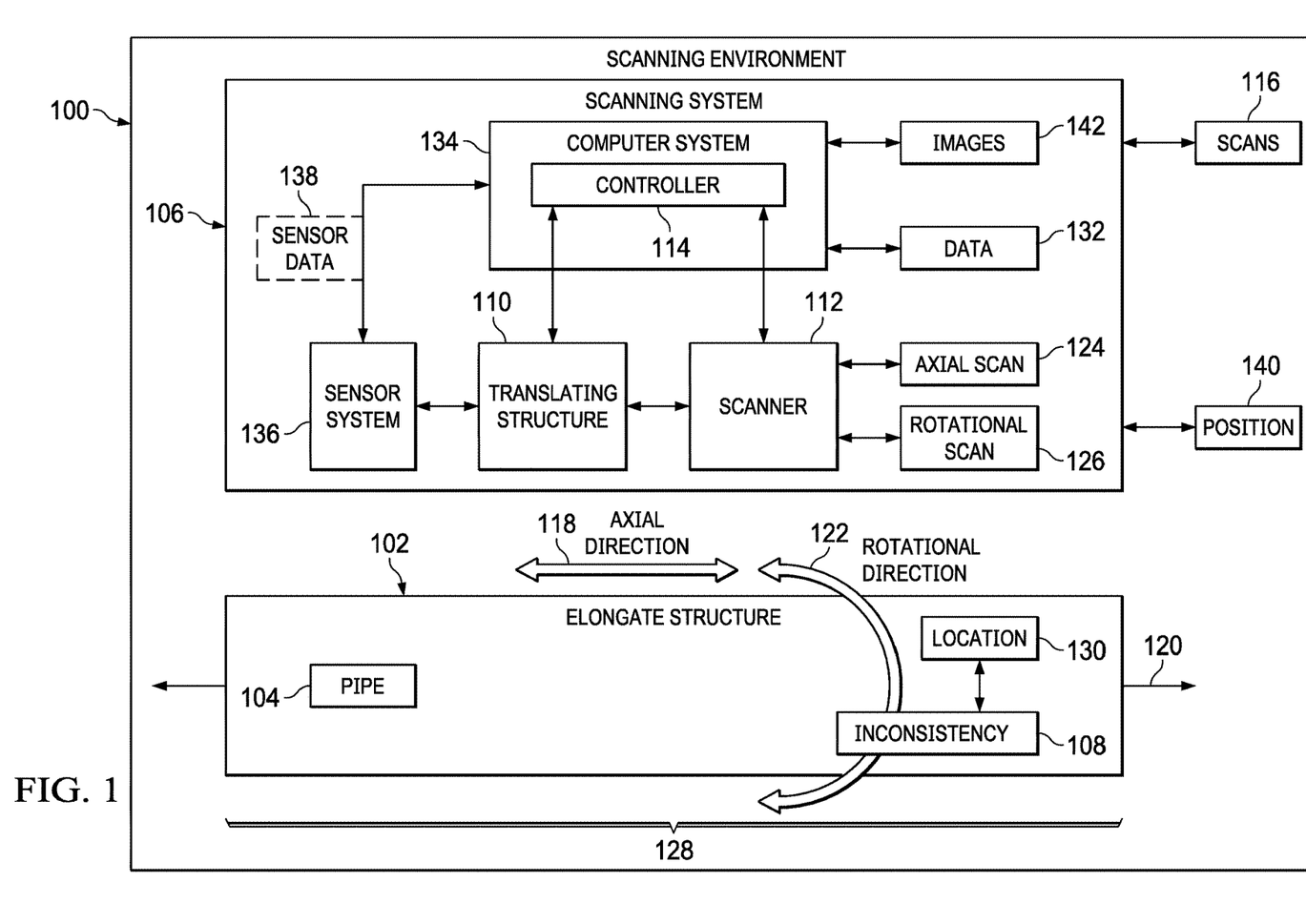
FIG. 1 is an illustration of a block diagram of a scanning environment in accordance with an illustrative embodiment.

With reference now to the figures and, specifically, with reference to FIG. 1, an illustration of a block diagram of a scanning environment is depicted in accordance with an illustrative embodiment. As depicted, scanning environment 100 includes elongate structure 102. In this illustrative example, elongate structure 102 takes the form of pipe 104. Pipe 104 carries various types of materials. For example, pipe 104 may carry at least one of a liquid, a gas, crude petroleum, refined petroleum, hydrogen, a fuel, oil, water, wine, beer, a natural gas, a biofuel, or other types of materials.

As used herein, the phrase "at least one of," when used with a list of items, means different combinations of one or more of the listed items may be used, and only one of each item in the list may be needed. In other words, "at least one of" means any combination of items and number of items may be used from the list, but not all of the items in the list are required. The item may be a particular object, a thing, or a category.

For example, without limitation, "at least one of item A, item B, or item C" may include item A, item A and item B, or item B. This example also may include item A, item B, and item C, or item B and item C. Of course, any combinations of these items may be present. In some illustrative examples, "at least one of" may be, for example, without limitation, two of item A; one of item B; and ten of item C; four of item B and seven of item C; or other suitable combinations.

In this illustrative example, pipe 104 may be inspected using scanning system 106. Scanning system 106 is used to determine whether inconsistency 108 is present within pipe 104.

Inconsistency 108 is indicated by an unexpected result from elongate structure 102. For example, the unexpected result may be a value that is greater or less than a threshold. The unexpected result may be a value that is outside of a desired range.

Inconsistency 108 may take a number of different forms. For example, inconsistency 108 may be selected from a group comprising corrosion, thinning walls, an out-of-tolerance welding, an out-of-tolerance deposit, scale, a crack, and other undesired results.

In this illustrative example, scanning system 106 includes a number of different components. As depicted, scanning system 106 includes translating structure 110, scanner 112, and controller 114. Scanning system 106 is configured to perform scans 116 automatically. In other words, the need for a human operator to move scanning system 106 on elongate structure 102 is unnecessary.

As depicted, translating structure 110 is a physical hardware structure. Translating structure 110 is configured to move axially and rotationally along elongate structure 102. Translating structure 110 moves in axial direction 118 by moving in a direction coinciding with axis 120 extending centrally through pipe 104. Pipe 104 may have many axes through curves and bins in pipe 104. Translating structure 110 moves in rotational direction 122 by rotating on pipe 104 around axis 120. As depicted, translating structure 110 may be selected from a group comprising a motorized arm, a crawler arm, a track-based arm, and some other suitable type of structure that moves axially and rotationally.

In the illustrative example, scanner 112 is connected to translating structure 110. As used herein, a first component, scanner 112, "connected to" a second component, translating structure 110, means that the first component can be connected directly or indirectly to the second component. In other words, additional components may be present between the first component and the second component. The first component is considered to be indirectly connected to the second component when one or more additional components are present between the two components. When the first component is directly connected to the second component, no additional components are present between the two components.

As depicted, scanner 112 may perform scans 116 using a number of different types of scanning techniques. For example, scanner 112 may be selected from at least one of an x-ray scanning system, a backscatter x-ray system, or a through transmission x-ray system.

In this example, controller 114 is in communication with translating structure 110 and scanner 112. As depicted, controller 114 controls translating structure 110 to move axially along elongate structure 102 while scanner 112 performs axial scan 124 of elongate structure 102 and controls translating structure 110 to move rotationally around elongate structure 102 while scanner 112 performs rotational scan 126 of elongate structure 102.

Controller 114 enables automated scanning of elongate structure 102 in axial direction 118 for axial scan 124 and rotational direction 122 for rotational scan 126. In this manner, automated inspection of elongate structure 102 is performed without using a human operator.

During operation of scanning system 106, controller 114 moves translating structure 110 axially along length 128 of elongate structure 102 and monitors for inconsistencies during axial scan 124 of elongate structure 102. As depicted, controller 114 moves translating structure 110 rotationally about elongate structure 102 in location 130 where inconsistency 108 is detected. Further, controller 114 detects data 132 during rotational scan 126 of elongate structure 102 at location 130.

In one illustrative example, translating structure 110 moves along length 128 of elongate structure 102 and moves axially to return to location 130 after completing axial scan 124 of elongate structure 102. Additionally, translating structure 110 moves rotationally at location 130 and performs rotational scan 126 at location 130. In another illustrative example, translating structure 110 halts moving axially along length 128 of elongate structure 102 at location 130 and moves rotationally around elongate structure 102 at location 130 while rotational scan 126 is performed. Rotational scan 126 may be performed at a slower speed, with data 132 being gathered in a manner that results in a higher degree of resolution for generating images 142 of location 130.

Controller 114 may be implemented in software, hardware, firmware, or a combination thereof. When software is used, the operations performed by controller 114 may be implemented in program code configured to run on hardware, such as a processor unit. When firmware is used, the operations performed by controller 114 may be implemented in program code and data and stored in persistent memory to run on a processor unit. When hardware is employed, the hardware may include circuits that operate to perform the operations in controller 114.

In the illustrative examples, the hardware may take a form selected from at least one of a circuit system, an integrated circuit, an application specific integrated circuit (ASIC), a programmable logic device, or some other suitable type of hardware configured to perform a number of operations. With a programmable logic device, the device may be configured to perform the number of operations. The device may be reconfigured at a later time or may be permanently configured to perform the number of operations.

Programmable logic devices include, for example, a programmable logic array, a programmable array logic, a field programmable logic array, a field programmable gate array, and other suitable hardware devices. Additionally, the processes may be implemented in organic components integrated with inorganic components and may be comprised entirely of organic components excluding a human being. For example, the processes may be implemented as circuits in organic semiconductors. In this illustrative example, pipe 104 may be inspected using scanning system 106. Scanning system 106 is used to determine whether inconsistency 108 is present within pipe 104.

In the illustrative example, controller 114 may be implemented as a component in computer system 134. Computer system 134 may be located on translating structure 110, scanner 112, some combination thereof, or in a remote location from these components but in communication with the components. In yet another illustrative example, a portion of computer system 134 may be located on translating structure 110, scanner 112, or a combination thereof, while another portion of computer system 134 is in a remote location to these components.

Computer system 134 is a physical hardware system and includes one or more data processing systems. When more than one data processing system is present, the data processing systems are in communication with each other using a communications medium. The communications medium may be a network. The data processing systems may be selected from at least one of a computer, a server computer, a tablet, or some other suitable data processing system.

In one illustrative example, one or more technical solutions are present that overcome a technical problem with scanning an insulated pipe for inconsistencies with a desired level of efficiency that reduces cost and time. As a result, one or more technical solutions provide a technical effect of more efficiently scanning an elongate structure, such as a pipe, using a scanning system that moves and scans axially and rotationally. One or more technical solutions provide a technical effect in which automated scanning is performed on elongate structures, such as pipes. Further, automated analysis of information gathered in an axial scan is used to control scanning system 106 to perform a rotational scan at selected locations where inconsistencies are detected. This type of automated analysis may reduce the time and expense involved in inspecting elongate structures, such as pipes.

Further, in the illustrative example, one or more technical solutions provide a technical effect in which placing or attaching external guides or support is unnecessary. As a result, the cost and time for inspecting elongate structure 102 may be reduced, as compared to currently available techniques.

As a result, computer system 134 operates as a special purpose computer system in which controller 114 in computer system 134 enables controlling the operation of a scanning system, such as a mobile scanning arm performing axial and rotational scans. In particular, controller 114 transforms computer system 134 into a special purpose computer system, as compared to currently available general computer systems that do not have controller 114.

Figure 2:
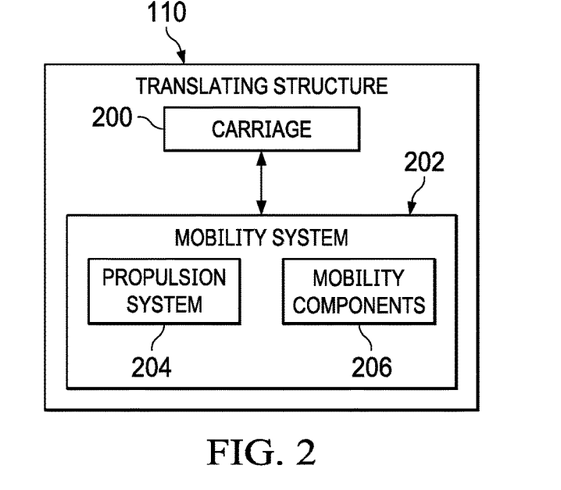
FIG. 2 is an illustration of a block diagram of a translating structure in accordance with an illustrative embodiment.

Turning next to FIG. 2, an illustration of a block diagram of a translating structure is depicted in accordance with an illustrative embodiment. In the illustrative examples, the same reference numeral may be used in more than one figure. This reuse of a reference numeral in different figures represents the same element in the different figures.

In the illustrative example, translating structure 110 includes a number of different components. As depicted, translating structure 110 comprises carriage 200 and mobility system 202.

In this example, carriage 200 is a physical structure that is configured to attach itself to elongate structure 102. For example, carriage 200 holds scanning system 106 on elongate structure 102 such that mobility system 202 is able to move carriage 200 axially and rotationally with respect to elongate structure 102.

As depicted, mobility system 202 comprises propulsion system 204 and mobility components 206. These units are selected to move carriage 200 axially and rotationally. Propulsion system 204 may be an electrically controlled propulsion system. Propulsion system 204 may be, for example, without limitation, selected from at least one of an internal combustion engine, an electric engine, or some other suitable propulsion system.

Mobility components 206 provide carriage 200 with the capability to move in a number of directions. Mobility components 206 may be comprised of at least one of a roller, a wheel, a holonomic wheel, a track, or other suitable components. As used herein, a holonomic wheel (or an omni wheel) is one that is capable of moving in multiple directions across a surface.

The illustrations of scanning environment 100 in FIG. 1 and the different components in FIG. 1 and FIG. 2 are not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, in FIG. 1, elongate structure 102 may take other forms other than pipe 104. In other illustrative examples, elongate structure 102 may be selected from one of a drum, a conduit, a structural cable, a stringer, a structural beam, a wind turbine blade, a station, a piling, and other suitable types of elongate structures.

As another example, scanning system 106 also may include sensor system 136. In this illustrative example, sensor system 136 is in communication with controller 114. Sensor system 136 may be connected to translating structure 110 or may be in a number of locations.

Sensor system 136 may be comprised of at least one of an encoder, a camera, an inertial measurement unit (IMU), an accelerometer, a global positioning system (GPS) unit, a gyroscope, or some other suitable type of sensor. In this illustrative example, sensor system 136 generates sensor data 138 that is used to determine position 140 of scanning system 106. Position 140 may comprise a three-dimensional location of translating structure 110, scanner 112, or some combination thereof. The three-dimensional location may be described using Cartesian coordinates, polar coordinates, or some other coordinate system.

In another illustrative example, position 140 may define an axial position along length 128 of elongate structure 102. This axial position may be identified using an encoder or a laser distance meter.

Position 140 also may include an orientation of one or both of these components. The orientation may be described in a number of different ways. For example, the orientation may be described using yaw, pitch, roll, a vector, or some other suitable system. In another example, a rotational position around elongate structure 102 may be identified using an encoder.

As another example, scanner 112 may also be configured to use other types of energy in addition to or in place of x-rays. For example, scanner 112 may be configured to direct energy at elongate structure 102 and detect the response to the energy directed at elongate structure 102, in which the energy is selected from a group comprising an x-ray, ultrasonic radiation, ultraviolet radiation, electromagnetic radiation, infrared radiation, microwave radiation, and other suitable types of energy.

Figure 3:
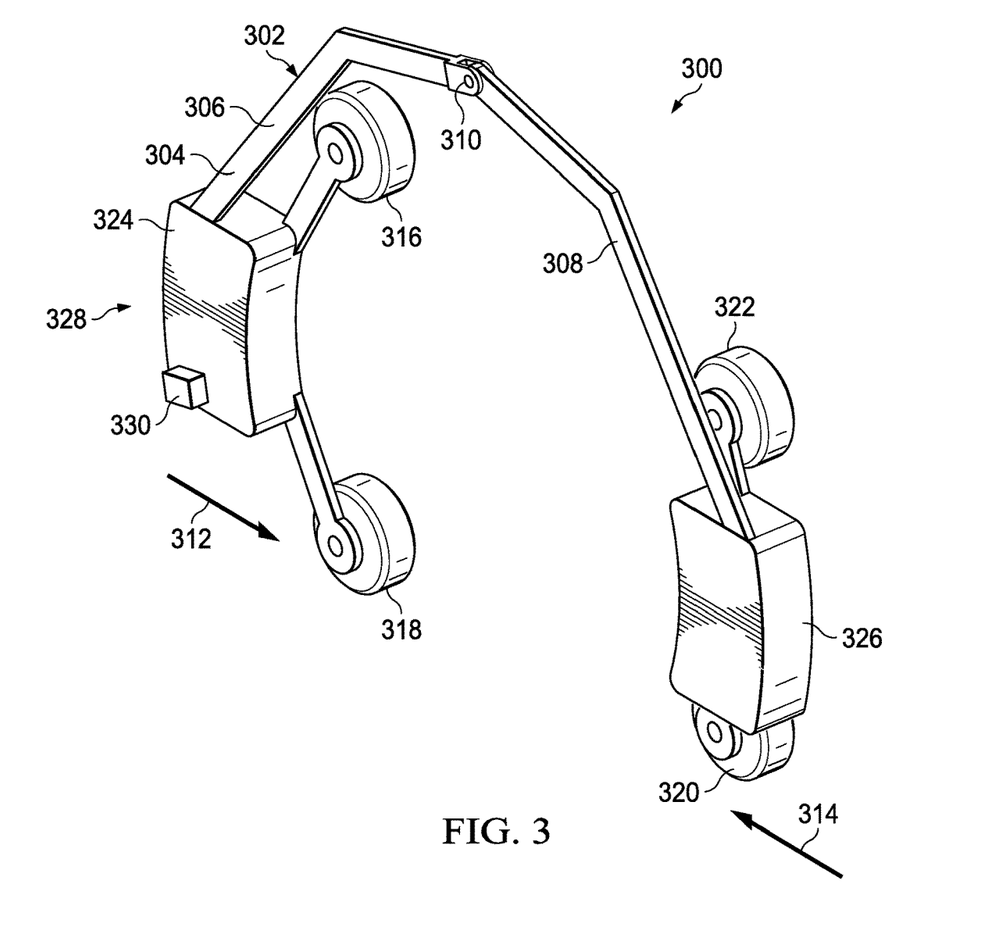
FIG. 3 is an illustration of a scanning system in accordance with an illustrative embodiment.

With reference now to FIG. 3, an illustration of a scanning system is depicted in accordance with an illustrative embodiment. In this illustrative example, scanning system 300 is an example of one physical implementation for scanning system 106 shown in block form in FIG. 1. As depicted, scanning system 300 takes the form of mobile scanning arm 302. Mobile scanning arm 302 has a number of different components. In this illustrative example, mobile scanning arm 302 includes carriage 304, which is an example of one physical implementation for carriage 200 in FIG. 2 for translating structure 110 shown in FIG. 1 and FIG. 2.

In this illustrative example, carriage 304 includes structural member 306, structural member 308, and biased joint 310. Biased joint 310 connects structural member 306 and structural member 308 to each other. Biased joint 310 causes structural member 306 to be biased in the direction of arrow 312 and structural member 308 to be biased in the direction of arrow 314. This biasing is designed to allow carriage 304 to clamp itself to a pipe or some other elongate structure for scanning operations.

Biased joint 310 may be implemented using a number of different mechanisms. For example, biased joint 310 may be a spring-loaded joint, a hydraulic piston, a screw actuator, a slide and snap adjustment system, or some other suitable mechanism.

Mobile scanning arm 302 includes holonomic wheel unit 316 (e.g. a unit including a holonomic wheel), holonomic wheel unit 318, holonomic wheel unit 320, and holonomic wheel unit 322. These wheel units are examples of components in mobility system 202 shown in block form in FIG. 2.

As depicted, holonomic wheel unit 316 and holonomic wheel unit 318 are connected to housing 324. Holonomic wheel unit 320 and holonomic wheel unit 322 are connected to housing 326. These wheel units include motors as well as wheels, and represent an implementation for propulsion system 204 and mobility components 206 in FIG. 2. Holonomic wheel unit 316, holonomic wheel unit 318, holonomic wheel unit 320, and holonomic wheel unit 322 allow for independent rotational movement and axial movement from the same set of wheel units.

As depicted, scanner 328 is located within at least one of housing 324 or housing 326 of mobile scanning arm 302. In this illustrative example, scanner 328 takes the form of at least one of a backscatter x-ray system or a through transmission x-ray system.

In this example, controller 330 is located within housing 324 and controls the operation of scanning system 300. For example, controller 330 controls the movement of mobile scanning arm 302 and the operation of scanner 328 in performing scans.

Figure 4:
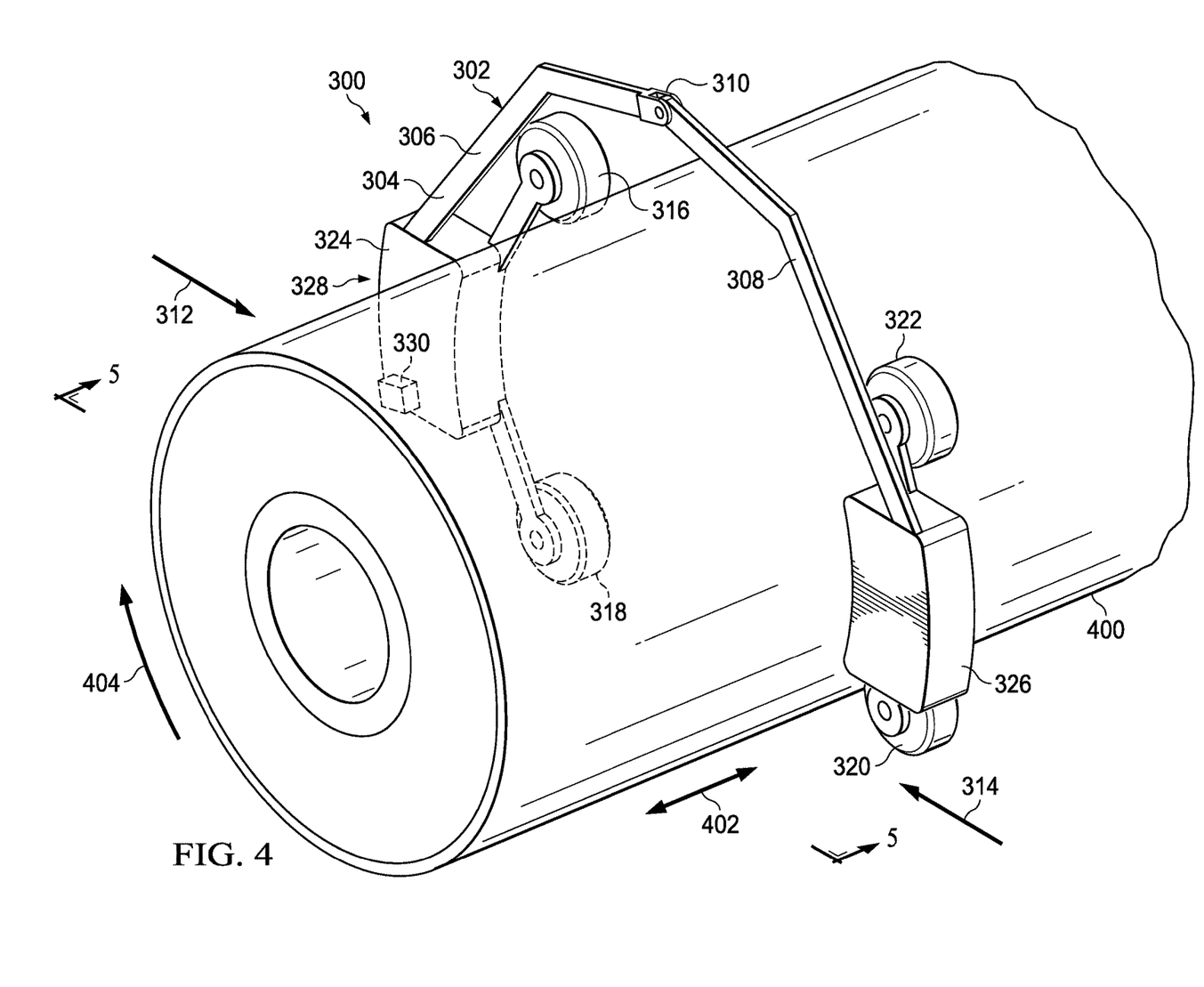
FIG. 4 is an illustration of a mobile scanning arm attached to a pipe in accordance with an illustrative embodiment.

With reference now to FIG. 4, an illustration of a mobile scanning arm attached to a pipe is depicted in accordance with an illustrative embodiment. In this illustrative example, mobile scanning arm 302 is shown as clamped on insulated pipe 400. Mobile scanning arm 302 may move axially as shown by arrow 402 and rotationally as shown by arrow 404 to scan insulated pipe 400.

Figure 5:
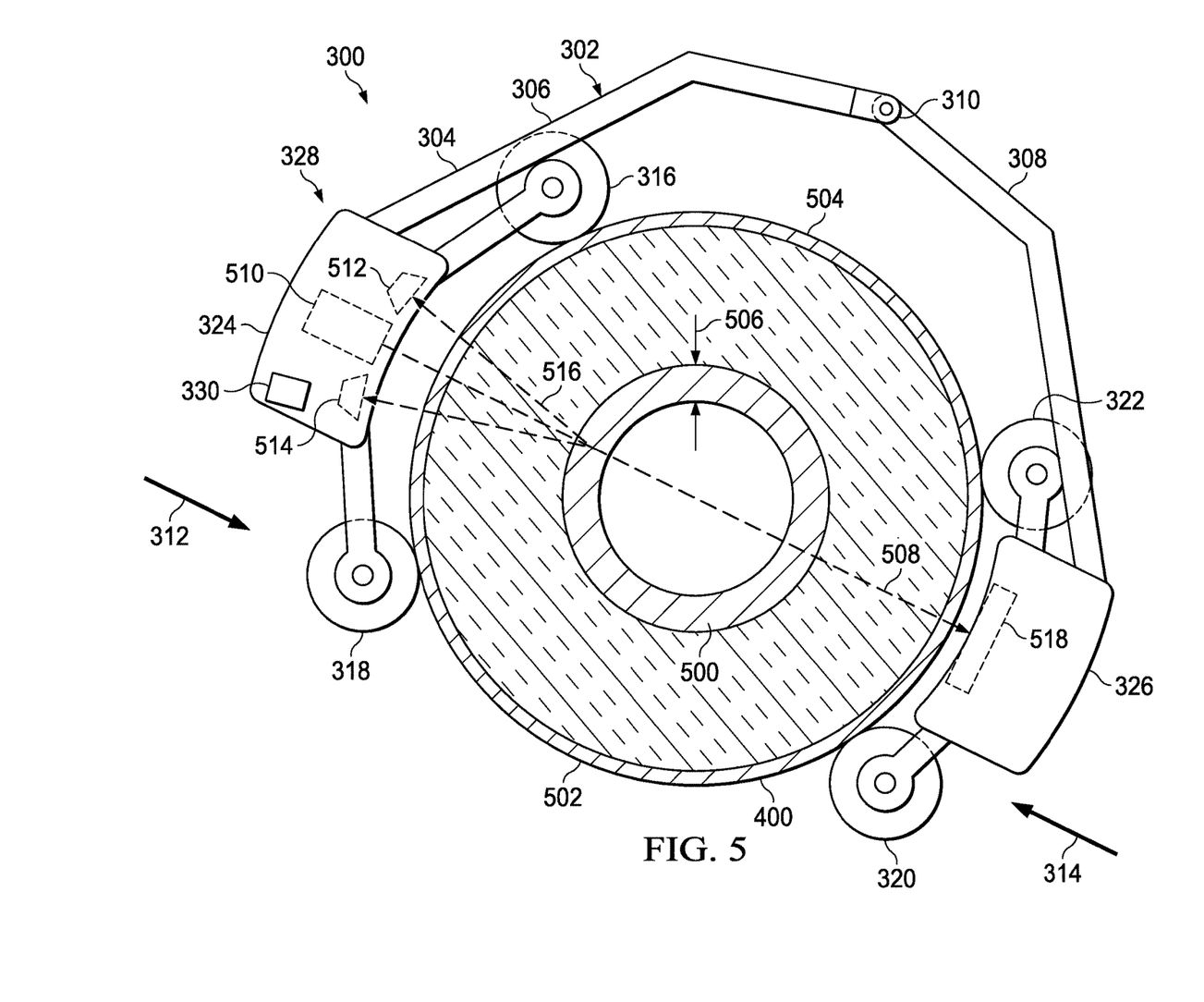
FIG. 5 is an illustration of a cross-sectional view of an insulated pipe with a mobile scanning arm in accordance with an illustrative embodiment.

With reference next to FIG. 5, an illustration of a cross-sectional view of an insulated pipe with a mobile scanning arm is depicted in accordance with an illustrative embodiment. As depicted, a cross-sectional view of pipe 400 with mobile scanning arm 302 is shown from a cross-section taken along separated lines 5-5 in FIG. 4.

As depicted in this example, insulated pipe 400 includes pipe 500 and insulation 502. As seen in this illustrative example, holonomic wheel unit 316, holonomic wheel unit 318, holonomic wheel unit 320, and holonomic wheel unit 322 all touch surface 504 on pipe 400.

In this illustrative example, mobile scanning arm 302 is configured to scan pipe 500 within insulation 502 for inconsistencies. Inconsistencies may be detected by identifying wall thickness 506 of pipe 500. Wall thickness 506 is identified using x-rays 508 emitted from scanner 328.

As depicted, scanner 328 includes x-ray source 510, detector 512, and detector 514, all shown using dashed lines within housing 324. In this illustrative example, x-ray source 510 is a pinhole x-ray source. As depicted, detector 512 and detector 514 are solid state detectors. The solid-state detectors may be, for example, semiconductor detectors that convert x-ray photons to electrical charge in a manner that allows for a digital image to be generated.

Detector 512 and detector 514 detect backscatter 516 from pipe 500 in response to x-rays 508. The detection of backscatter 516 may be used to identify wall thickness 506 of pipe 500.

Further, scanner 328 also may be a through transmission x-ray system in addition to a backscatter x-ray system. With this type of implementation, detector 518 is shown using dashed lines within housing 326. Detector 518 may be a multiple pixel imaging system for generating images using through transmission x-rays emitted from x-ray source 510.

Figure 6:
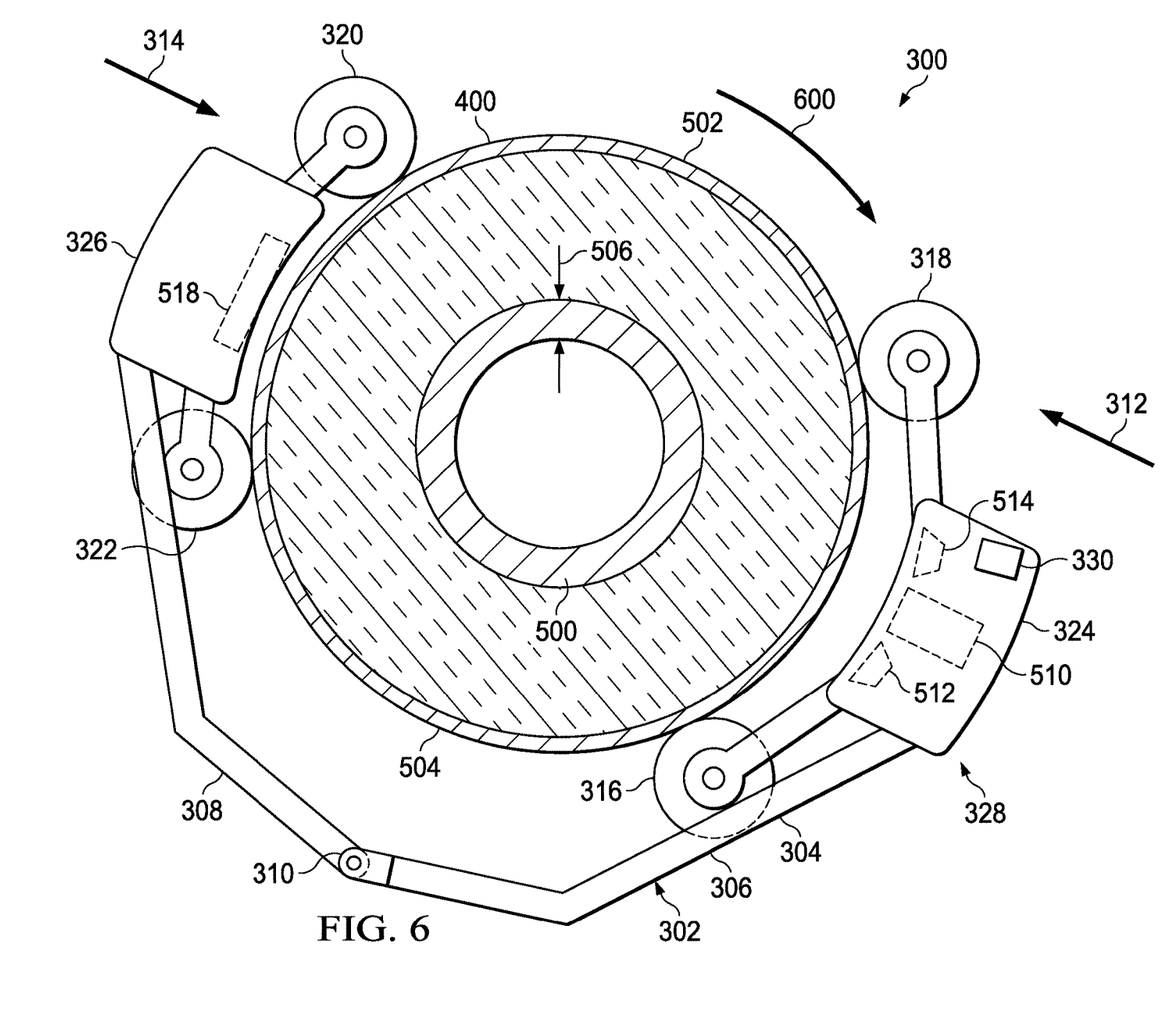
FIG. 6 is an illustration of a cross-sectional view of an insulated pipe with a mobile scanning arm in accordance with an illustrative embodiment.

Turning to FIG. 6, an illustration of a cross-sectional view of an insulated pipe with a mobile scanning arm is depicted in accordance with an illustrative embodiment. In this figure, mobile scanning arm 302 has rotated about insulated pipe 400 in the direction of arrow 600. In this illustrative example, mobile scanning arm 302 has rotated about 180 degrees.

Scanner 328 on mobile scanning arm 302 performs a rotational scan while rotating. A rotational scan may be performed when rotating any number of degrees, such as between about zero degrees and about 360 degrees. The rotational scan can detect parameters or conditions selected from at least one of insulation, moisture, corrosion, fluid level, water accumulation, small leaks, or other parameters or conditions.

The illustration of scanning system 300 in FIGS. 3-6 is not meant to limit the manner in which other scanning systems may be implemented. Wheels that may be angled may be used instead of holonomic wheel units in mobile scanning arm 302. In yet another illustrative example, mobile scanning arm 302 may include a crawler that is connected to carriage 304. The crawler may move axially while carriage 304 moves rotationally.

Figure 7:
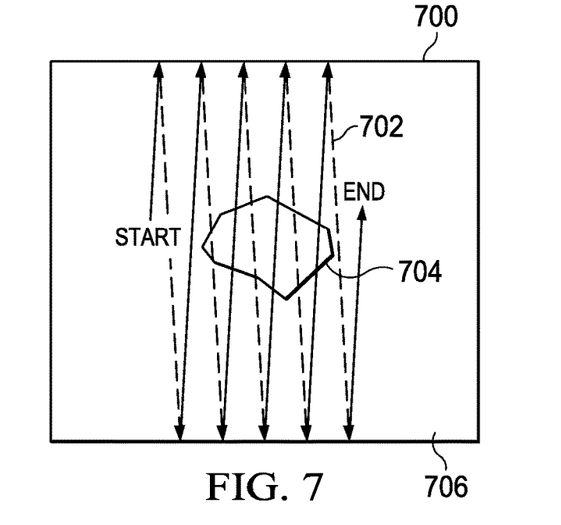
FIG. 7 is an illustration of a scanning path in accordance with an illustrative embodiment.

With reference now to FIG. 7, an illustration of a scanning path is depicted in accordance with an illustrative embodiment. In this illustrative example, pipe 700 is shown with helical scanning path 702.

Helical scanning path 702 is an example of a path that may be used by scanning system 300 in FIGS. 3-6 to perform an inspection of pipe 700. Helical scanning path 702 includes both axial and rotational movement of a scanning system, such as mobile scanning arm 302 shown in FIGS. 3-6.

In this illustrative example, inconsistency 704 is present within pipe 700. As depicted, inconsistency 704 is a thinning of wall 706 of pipe 700 due to corrosion. Helical scanning path 702 provides an ability to detect inconsistency 704.

In this illustrative example, a reversal in direction of helical scanning path 702 may be used to reduce data gaps. The reverse direction may be made such that an overlap of one line spacing in a scan occurs when reversing the rotational scan direction.

Figure 8:
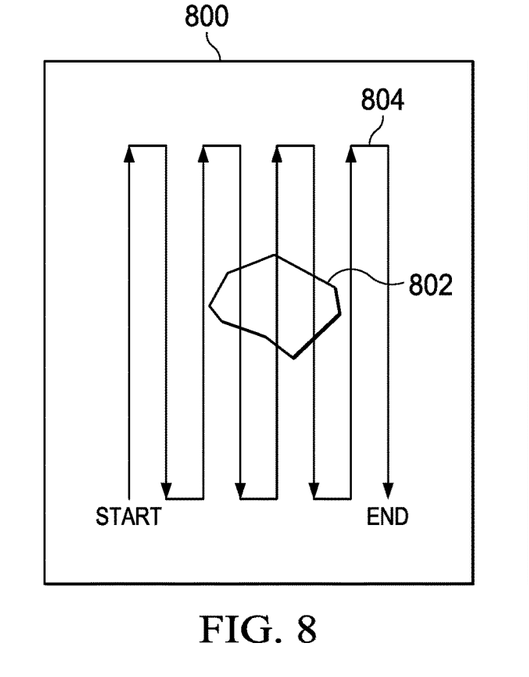
FIG. 8 is an illustration of a scanning path in accordance with an illustrative embodiment.

Turning to FIG. 8, an illustration of a scanning path is depicted in accordance with an illustrative embodiment. As depicted, pipe 800 is shown with inconsistency 802. Raster scanning path 804 is an example of a path that may be used by scanning system 300 in FIGS. 3-6 to perform an inspection of pipe 800.

In this illustrative example, raster scanning path 804 provides for a combination of rotational and axial scan. In this illustrative example, raster scanning path 804 covers a portion of the circumference of pipe 800.

Figure 9:
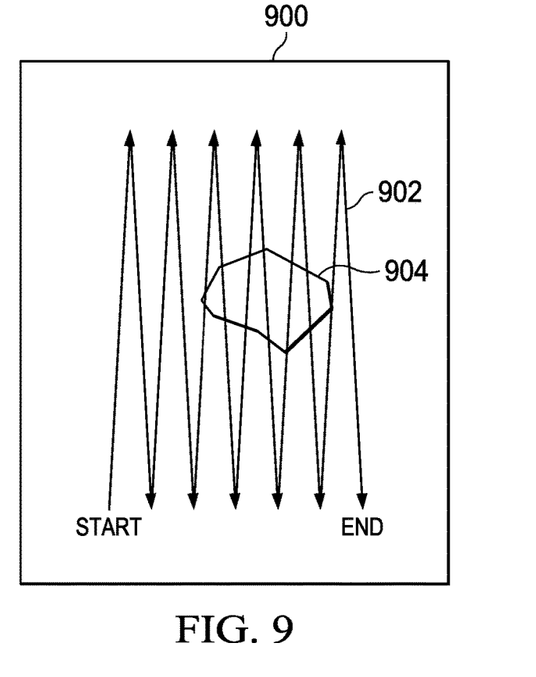
FIG. 9 is an illustration of a scanning path in accordance with an illustrative embodiment.

With reference to FIG. 9, an illustration of a scanning path is depicted in accordance with an illustrative embodiment. As depicted, pipe 900 is shown with sawtooth scanning path 902. Sawtooth scanning path 902 is an example of a path that may be used by scanning system 300 in FIGS. 3-6 to perform an inspection of pipe 900.

Sawtooth scanning path 902 provides for a combination of a rotational scan and an axial scan. In this illustrative example, sawtooth scanning path 902 only covers a portion of the circumference of pipe 900. In this example, inconsistency 904 may be detected through scans performed using sawtooth scanning path 902. A reverse in the direction of sawtooth scanning path 902 also may be used to reduce gaps in data.

The illustrations of scanning paths in FIGS. 7-9 are provided as examples of some patterns of paths that a scanning system, such as mobile scanning arm 302, may use to perform scans of a pipe. These illustrations are not meant to limit the manner in which mobile scanning arm 302 may be implemented or move to scan a pipe. For example, raster scanning path 804 in FIG. 8 and sawtooth scanning path 902 in FIG. 9 may be performed for a full pipe inspection, in which these paths encompass the entire circumference of the pipe for a rotational portion of the scan.

In this manner, translating structure 110, shown in block form in FIG. 1, may move using a number of different types of patterns for paths. In the above examples, translating structure 110 moves in at least one of helical scanning path 702, raster scanning path 804, or a sawtooth scanning path 902.

Figure 10:
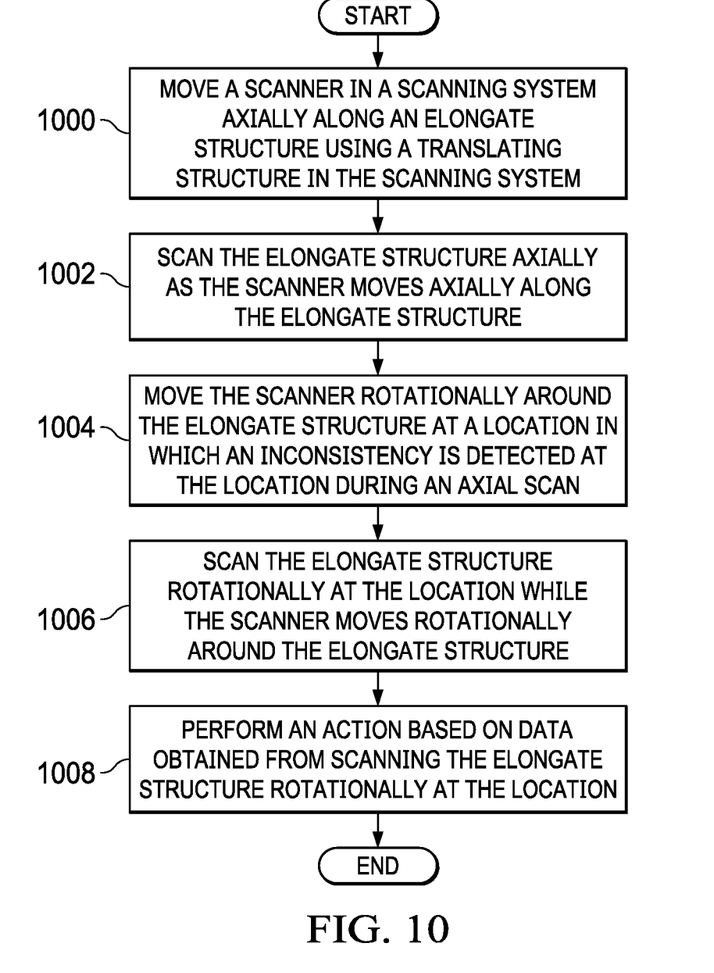
FIG. 10 is an illustration of a flowchart of a process for scanning an elongate structure in accordance with an illustrative embodiment.

Turning next to FIG. 10, an illustration of a flowchart of a process for scanning an elongate structure is depicted in accordance with an illustrative embodiment. The process illustrated in this figure may be implemented in scanning system 106 shown in block form in FIG. 1. The process may be implemented in at least one of program code, hardware, firmware, or some combination thereof in controller 114 shown in block form in FIG. 1. The process is an automated process to inspect an elongate structure, such as a pipe.

The process begins by moving a scanner in a scanning system axially along an elongate structure using a translating structure in the scanning system (operation 1000). The process scans the elongate structure axially as the scanner moves axially along the elongate structure (operation 1002). The axial scan may be performed in a manner that generates less data. For example, the axial scan may be used to determine whether a threshold value for wall thickness has been exceeded to indicate the presence of an inconsistency.

The process moves the scanner rotationally around the elongate structure at a location in which an inconsistency is detected at the location during an axial scan (operation 1004). The process scans the elongate structure rotationally at the location while the scanner moves rotationally around the elongate structure (operation 1006). The rotation scan may be performed in a manner that generates more data than in the axial scan. The additional data may be used to generate an image or provide sufficient information to analyze the inconsistency.

The process performs an action based on data obtained from scanning the elongate structure rotationally at the location (operation 1008). The process terminates thereafter. In operation 1008, the action may take various forms. For example, the action may be selected from a group comprising generating an alert, halting use of the elongate structure, generating an image of the inconsistency, generating a log entry, identifying structural integrity, identifying fluid levels, identifying effectiveness of insulating materials, or other suitable actions.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent at least one of a module, a segment, a function, or a portion of an operation or step.

For example, one or more of the blocks may be implemented as program code, hardware, or a combination of the program code and hardware. When implemented in hardware, the hardware may, for example, take the form of integrated circuits that are manufactured or configured to perform one or more operations in the flowcharts or block diagrams. When implemented as a combination of program code and hardware, the implementation may take the form of firmware. Each block in the flowcharts or the block diagrams may be implemented using special purpose hardware systems that perform the different operations or combinations of special purpose hardware and program code run by the special purpose hardware.

In some alternative implementations of an illustrative embodiment, the function or functions noted in the blocks may occur out of the order noted in the figures. For example, in some cases, two blocks shown in succession may be performed substantially concurrently, or the blocks may sometimes be performed in the reverse order, depending upon the functionality involved. Also, other blocks may be added in addition to the illustrated blocks in a flowchart or block diagram.

For example, in FIG. 10, the process may move the scanner axially to return to the location after completing the axial scan of the elongate structure prior to moving the scanner rotationally to scan the elongate structure rotationally in operation 1004. As another example, the process may halt moving the scanner axially when the inconsistency is detected prior to moving the scanner rotationally to scan the object rotationally in operation 1004.

Figure 11:
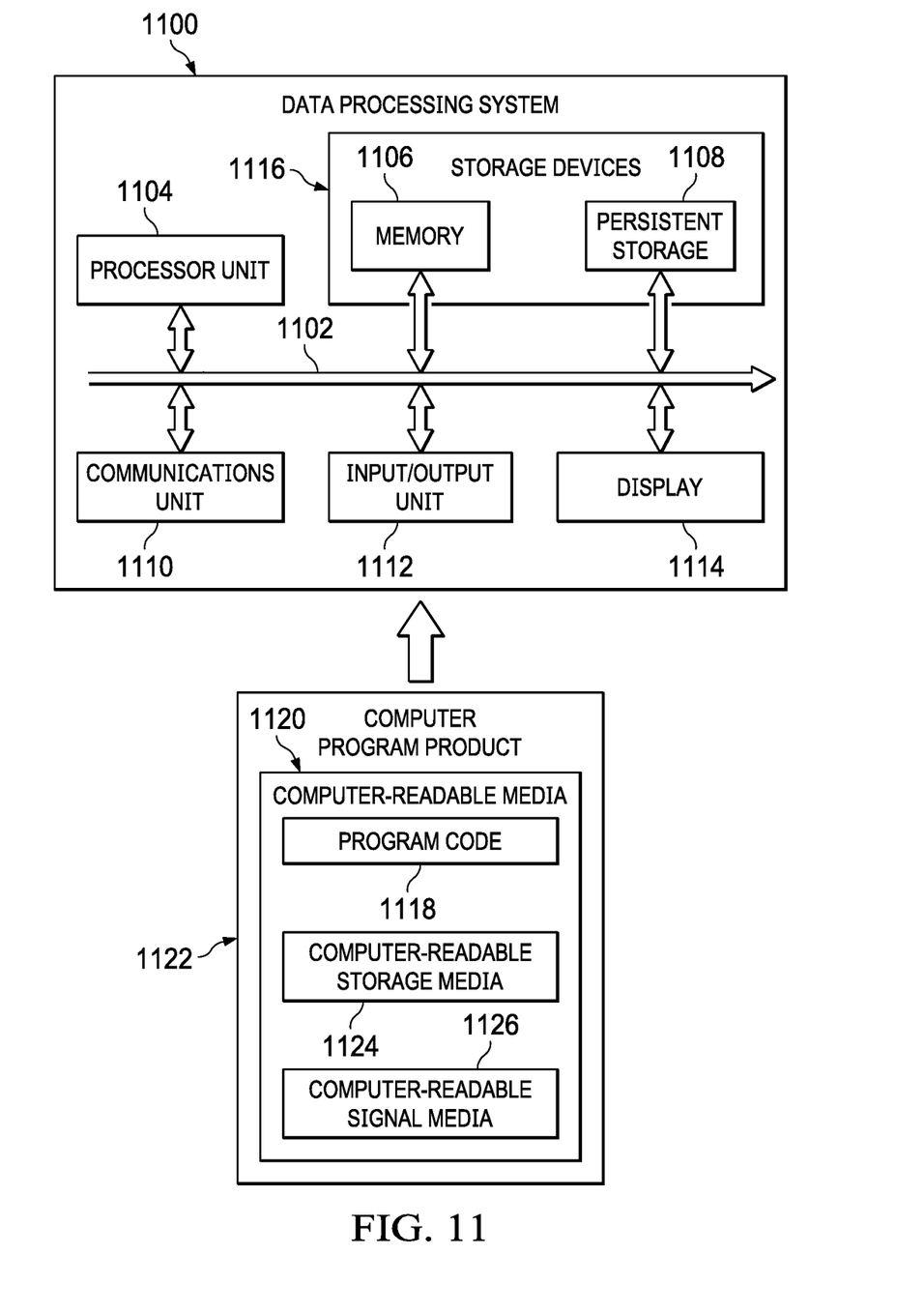
FIG. 11 is an illustration of a block diagram of a data processing system in accordance with an illustrative embodiment.

Turning now to FIG. 11, an illustration of a block diagram of a data processing system is depicted in accordance with an illustrative embodiment. Data processing system 1100 may be used to implement computer system 134 shown in block form in FIG. 1. In this illustrative example, data processing system 1100 includes communications framework 1102, which provides communications between processor unit 1104, memory 1106, persistent storage 1108, communications unit 1110, input/output (I/O) unit 1112, and display 1114. In this example, communications framework 1102 may take the form of a bus system.

Processor unit 1104 serves to execute instructions for software that may be loaded into memory 1106. Processor unit 1104 may be a number of processors, a multi-processor core, or some other type of processor, depending on the particular implementation.

Memory 1106 and persistent storage 1108 are examples of storage devices 1116. A storage device is any piece of hardware that is capable of storing information, such as, for example, without limitation, at least one of data, program code in functional form, or other suitable information either on a temporary basis, a permanent basis, or both on a temporary basis and a permanent basis. Storage devices 1116 may also be referred to as computer-readable storage devices, in these illustrative examples. Memory 1106, in these examples, may be, for example, a random-access memory or any other suitable volatile or non-volatile storage device. Persistent storage 1108 may take various forms, depending on the particular implementation.

For example, persistent storage 1108 may contain one or more components or devices. For example, persistent storage 1108 may be a hard drive, a solid state hard drive, a flash memory, a rewritable optical disk, a rewritable magnetic tape, or some combination of the above. The media used by persistent storage 1108 also may be removable. For example, a removable hard drive may be used for persistent storage 1108.

Communications unit 1110, in these illustrative examples, provides for communications with other data processing systems or devices. In these illustrative examples, communications unit 1110 is a network interface card.

Input/output unit 1112 allows for input and output of data with other devices that may be connected to data processing system 1100. For example, input/output unit 1112 may provide a connection for user input through at least one of a keyboard, a mouse, or some other suitable input device. Further, input/output unit 1112 may send output to a printer. Display 1114 provides a mechanism to display information to a user.

Instructions for at least one of the operating system, applications, or programs may be located in storage devices 1116, which are in communication with processor unit 1104 through communications framework 1102. The processes of the different embodiments may be performed by processor unit 1104 using computer-implemented instructions, which may be located in a memory, such as memory 1106.

These instructions are referred to as program code, computer-usable program code, or computer-readable program code that may be read and executed by a processor in processor unit 1104. The program code in the different embodiments may be embodied on different physical or computer-readable storage media, such as memory 1106 or persistent storage 1108.

Program code 1118 is located in a functional form on computer-readable media 1120 that is selectively removable and may be loaded onto or transferred to data processing system 1100 for execution by processor unit 1104. Program code 1118 and computer-readable media 1120 form computer program product 1122 in these illustrative examples. In one example, computer-readable media 1120 may be computer-readable storage media 1124 or computer-readable signal media 1126.

In these illustrative examples, computer-readable storage media 1124 is a physical or tangible storage device used to store program code 1118 rather than a medium that propagates or transmits program code 1118.

Alternatively, program code 1118 may be transferred to data processing system 1100 using computer-readable signal media 1126. Computer-readable signal media 1126 may be, for example, a propagated data signal containing program code 1118. For example, computer-readable signal media 1126 may be at least one of an electromagnetic signal, an optical signal, or any other suitable type of signal. These signals may be transmitted over at least one of communications links, such as wireless communications links, optical fiber cable, coaxial cable, a wire, or any other suitable type of communications link.

The different components illustrated for data processing system 1100 are not meant to provide architectural limitations to the manner in which different embodiments may be implemented. The different illustrative embodiments may be implemented in a data processing system including components in addition to or in place of those illustrated for data processing system 1100. Other components shown in FIG. 11 can be varied from the illustrative examples shown. The different embodiments may be implemented using any hardware device or system capable of running program code 1118.

In one illustrative example, one or more technical solutions are present that overcome a technical problem with scanning an insulated pipe for inconsistencies with a desired level of efficiency that reduces cost and time. As a result, one or more technical solutions may provide a technical effect of more efficiently scanning an elongate structure, such as a pipe, using a scanning system that moves and scans axially and rotationally.

In addition, one or more technical solutions are present in which the technical effect of automatically scanning an elongate structure is achieved. Further, a technical effect is also present in which a need to place or attach external guidance or support is absent. In this manner, the inspection of the elongate structure, such as a pipe, may be performed more efficiently with less time and cost as compared to current techniques for pipe inspections.

The description of the different illustrative embodiments has been presented for purposes of illustration and description and is not intended to be exhaustive or limited to the embodiments in the form disclosed. The different illustrative examples describe components that perform actions or operations. In an illustrative embodiment, a component may be configured to perform the action or operation described. For example, the component may have a configuration or design for a structure that provides the component an ability to perform the action or operation that is described in the illustrative examples as being performed by the component.

Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A scanning system comprising:
   a translating structure configured to move axially and rotationally on an elongate structure;
   a scanner connected to the translating structure; and
   a controller in communication with the translating structure and the scanner, wherein the controller is configured to:
   control the translating structure to move axially along the elongate structure while the scanner performs an axial scan of the elongate structure; and
   control the translating structure to move rotationally around the elongate structure while the scanner performs a rotational scan of the elongate structure when an inconsistency is detected at a location on the elongate structure.

2. The scanning system of claim 1, wherein the controller is configured to move the translating structure axially along a length of the elongate structure and is configured to monitor for inconsistencies during the axial scan of the elongate structure.

3. The scanning system of claim 2, wherein the controller is configured to detect data during the rotational scan of the elongate structure at the location where the inconsistency is detected, wherein the rotational scan is performed at a slower speed than the axial scan to increase resolution.

4. The scanning system of claim 2, wherein the translating structure is configured to:
   move along the length of the elongate structure;
   move axially to return to the location after completing the axial scan of the elongate structure; and
   move rotationally at the location where the inconsistency is detected to perform the rotational scan at the location.

5. The scanning system of claim 2, wherein the translating structure is configured to halt moving axially along the length of the elongate structure at the location and is configured to move rotationally around the elongate structure at the location while the rotational scan is performed.

6. The scanning system of claim 1, wherein the translating structure comprises:
   a carriage configured to attach itself to the elongate structure; and
   a mobility system configured to move the carriage axially and rotationally.

7. The scanning system of claim 6, wherein the carriage is configured to attach itself to the elongate structure such that that a wheel system contacts the elongate structure in a manner that allows the wheel system to move the carriage axially and rotationally.

8. The scanning system of claim 6, wherein the mobility system is comprised of at least one of a roller, a wheel, a holonomic wheel, or a track.

9. The scanning system of claim 1, wherein the translating structure moves in at least one of a helical scanning path, a raster scanning path, or a sawtooth scanning path.

10. The scanning system of claim 1, wherein the translating structure is selected from a group comprising a motorized arm, a crawler arm, and a track-based arm.

11. The scanning system of claim 1, wherein the scanner is comprised of at least one of an x-ray scanning system, a backscatter x-ray system, or a through transmission x-ray system.

12. The scanning system of claim 1, wherein the elongate structure is selected from one of a pipe, a drum, a conduit, a stringer, a structural beam, a wind turbine blade, a station, and a piling.

13. The scanning system of claim 1, wherein the scanner is configured to direct energy at the elongate structure and detect a response to the energy directed at the elongate structure, and wherein the energy is selected from a group comprising an x-ray, ultrasonic radiation, ultraviolet radiation, electromagnetic radiation, infrared radiation, and microwave radiation.

14. An x-ray scanning system comprising:
   a mobile scanning arm;
   an x-ray scanner; and a controller in communication with the mobile scanning arm and the x-ray scanner, wherein the controller is configured to:
- move the mobile scanning arm axially such that the x-ray scanner performs an axial scan of an elongate structure; and
- move the mobile scanning arm rotationally such that the x-ray scanner performs a rotational scan around the elongate structure when an inconsistency is detected at a location on the elongate structure.

15. The x-ray scanning system of claim 14, wherein the mobile scanning arm comprises:
- a carriage; and
- a mobility system configured to move the carriage axially and rotationally.

16. The x-ray scanning system of claim 15, wherein the carriage comprises:
- a first structural member;
- a second structural member; and
- a biased joint connecting the first structural member and the second structural member to each other, wherein the biased joint clamps the mobile scanning arm to a cylindrical object such that the mobility system contacts a surface of the cylindrical object in a manner that allows the mobility system to move the carriage axially and rotationally.

17. The x-ray scanning system of claim 16, wherein the mobility system comprises at least one of a wheel system, a roller, a wheel, or a holonomic wheel.

18. The x-ray scanning system of claim 14, wherein the x-ray scanner comprises at least one of a backscatter x-ray system or a through transmission x-ray system.

19. The x-ray scanning system of claim 14, wherein the mobile scanning arm is selected from a group comprising a motorized arm, a crawler arm, and a track-based arm.

20. A method for scanning an elongate structure, the method comprising:
- moving a scanner in a scanning system axially along the elongate structure using a translating structure in the scanning system;
- scanning the elongate structure axially as the scanner moves axially along the elongate structure;
- when an inconsistency is detected at a location on the elongate structure, moving the scanner rotationally around the elongate structure at the location in which the inconsistency is detected during the axial scan; and
- scanning the elongate structure rotationally at the location while the scanner moves rotationally around the elongate structure.

21. The method of claim 20 further comprising:
- performing an action based on data obtained from scanning the elongate structure rotationally at the location.

22. The method of claim 20 further comprising:
- moving the scanner axially to return to the location after completing the axial scan of the elongate structure prior to moving the scanner rotationally to scan the elongate structure rotationally.

23. The method of claim 20 further comprising:
- halting moving the scanner axially when the inconsistency is detected prior to moving the scanner rotationally to scan the elongate structure rotationally.

24. The method of claim 20, wherein the translating structure comprises a carriage configured to attach itself to the elongate structure and a wheel system configured to move the carriage axially and rotationally.

25. The method of claim 24, wherein the carriage is configured to attach itself to the elongate structure such that the wheel system contacts the elongate structure in a manner that allows the wheel system to move the carriage axially and rotationally.

26. The method of claim 20, wherein the translating structure moves in at least one of a helical scanning path, a raster scanning path, or a sawtooth scanning path.

27. The method of claim 20, wherein the translating structure is selected from one of a motorized arm, a crawler arm, and a track-based arm.

* * * * *